(12) United States Patent
Prandi et al.

(10) Patent No.: US 12,059,186 B2
(45) Date of Patent: *Aug. 13, 2024

(54) RESORPTIVE INTRAMEDULLARY IMPLANT BETWEEN TWO BONES OR TWO BONE FRAGMENTS

(71) Applicant: Stryker European Operations Holdings, LLC, Wilmington, DE (US)

(72) Inventors: Bernard Prandi, Rennes (FR); Marc Augoyard, Tassin la Demi Lune (FR); Thomas Ledermann, Eschenbach (CH); Tristan Meusnier, Saint-Etienne (FR); Jacques Peyrot, Tassin la Demi Lune (FR); Judith Fellmann, Stafa (CH)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 574 days.

This patent is subject to a terminal disclaimer.

(21) Appl. No.: 16/506,353

(22) Filed: Jul. 9, 2019

(65) Prior Publication Data

US 2019/0328433 A1 Oct. 31, 2019

Related U.S. Application Data

(60) Continuation of application No. 14/858,855, filed on Sep. 18, 2015, now Pat. No. 10,383,671, which is a (Continued)

(30) Foreign Application Priority Data

Sep. 9, 2008 (FR) ........................ 0856035

(51) Int. Cl.
*A61B 17/68* (2006.01)
*A61B 17/16* (2006.01)
(Continued)

(52) U.S. Cl.
CPC ...... *A61B 17/8605* (2013.01); *A61B 17/1655* (2013.01); *A61B 17/68* (2013.01);
(Continued)

(58) Field of Classification Search
CPC . A61B 17/8605; A61B 17/68; A61B 17/7233; A61B 17/7225; A61B 17/7283; A61F 2/4225; A61F 2/4241
See application file for complete search history.

(56) References Cited

U.S. PATENT DOCUMENTS

| 321,389 | A | * | 6/1885 | Schirmer | ................ F16B 15/06 |
| | | | | | 411/389 |
| 1,095,054 | A | | 4/1914 | Wiesenfeld | |

(Continued)

FOREIGN PATENT DOCUMENTS

| CA | 2551021 A1 | 3/2005 |
| CA | 2243699 C | 1/2006 |

(Continued)

OTHER PUBLICATIONS

EP Notification for Application No. 09741356.1 dated Feb. 12, 2015, 4 pages.
(Continued)

*Primary Examiner* — Ellen C Hammond
(74) *Attorney, Agent, or Firm* — Lerner David LLP

(57) ABSTRACT

The invention relates to a resorptive intramedullary implant between two bones or two bone fragments. The implant includes a single-piece body (1) having a generally elongate shape and having, at each end, areas for anchoring to the bone portions in question, characterized in that one of said areas (A1) has a cylindrical cross-section while the other area (A2) has a flat cross-section.

21 Claims, 4 Drawing Sheets

Related U.S. Application Data division of application No. 13/795,946, filed on Mar. 12, 2013, now Pat. No. 9,168,074, which is a continuation of application No. 12/918,105, filed as application No. PCT/FR2009/051658 on Sep. 2, 2009, now Pat. No. 8,414,583.

(51) Int. Cl.

| | | |
|---|---|---|
| A61B 17/72 | (2006.01) | |
| A61B 17/86 | (2006.01) | |
| A61B 17/88 | (2006.01) | |
| A61F 2/42 | (2006.01) | |
| A61B 17/00 | (2006.01) | |
| A61F 2/30 | (2006.01) | |

(52) U.S. Cl.
CPC .......... *A61B 17/7233* (2013.01); *A61B 17/88* (2013.01); *A61F 2/4225* (2013.01); *A61F 2/4241* (2013.01); *A61B 2017/00862* (2013.01); *A61B 2017/681* (2013.01); *A61B 17/7208* (2013.01); *A61B 17/7225* (2013.01); *A61B 17/7266* (2013.01); *A61B 17/7283* (2013.01); *A61B 2017/8655* (2013.01); *A61F 2002/30062* (2013.01); *A61F 2002/30563* (2013.01); *A61F 2002/30622* (2013.01); *A61F 2002/3085* (2013.01); *A61F 2002/30878* (2013.01); *A61F 2210/0004* (2013.01)

(56) References Cited

U.S. PATENT DOCUMENTS

| | | | |
|---|---|---|---|
| 2,128,005 | A | 8/1938 | Lombard |
| 2,208,848 | A | 7/1940 | Jorgensen |
| 2,531,911 | A | 11/1950 | Johnson |
| 3,338,689 | A | 8/1967 | Hetzel et al. |
| 3,462,765 | A | 8/1969 | Swanson |
| 3,466,669 | A | 9/1969 | Flatt |
| 3,593,342 | A | 7/1971 | Niebauer et al. |
| 3,646,654 | A | 3/1972 | Cervenka et al. |
| 3,681,786 | A | 8/1972 | Lynch |
| 3,739,403 | A | 6/1973 | Nicolle |
| 3,805,302 | A | 4/1974 | Mathys |
| 3,824,631 | A | 7/1974 | Burstein et al. |
| 3,875,594 | A | 4/1975 | Swanson |
| D243,716 | S | 3/1977 | Treace et al. |
| 4,091,806 | A | 5/1978 | Aginsky et al. |
| 4,158,893 | A | 6/1979 | Swanson |
| 4,204,284 | A | 5/1980 | Koeneman |
| 4,237,875 | A | 12/1980 | Termanini |
| 4,276,660 | A | 7/1981 | Laure |
| 4,364,382 | A | 12/1982 | Mennen |
| 4,367,562 | A | 1/1983 | Gauthier et al. |
| D277,509 | S | 2/1985 | Lawrence et al. |
| D277,784 | S | 2/1985 | Sgarlato et al. |
| 4,522,200 | A | 6/1985 | Stednitz |
| D284,099 | S | 6/1986 | Laporta et al. |
| 4,634,382 | A | 1/1987 | Kusano et al. |
| D291,731 | S | 9/1987 | Aikins |
| 4,759,768 | A | 7/1988 | Hermann et al. |
| 4,871,367 | A | 10/1989 | Christensen et al. |
| 4,955,916 | A | 9/1990 | Carignan et al. |
| 4,969,909 | A | 11/1990 | Barouk |
| 5,011,497 | A | 4/1991 | Persson et al. |
| 5,047,059 | A | 9/1991 | Saffar |
| 5,062,851 | A | 11/1991 | Branemark |
| 5,092,896 | A | 3/1992 | Meuli et al. |
| 5,108,443 | A | 4/1992 | Branemark |
| 5,133,761 | A | 7/1992 | Krouskop |
| 5,179,915 | A | 1/1993 | Cohen et al. |
| 5,190,546 | A | 3/1993 | Jervis |
| 5,207,712 | A | 5/1993 | Cohen |
| 5,326,364 | A | 7/1994 | Clift, Jr. et al. |
| 5,360,450 | A | 11/1994 | Giannini |
| 5,382,251 | A | 1/1995 | Hood et al. |
| 5,405,400 | A | 4/1995 | Linscheid et al. |
| 5,405,401 | A | 4/1995 | Lippincott, III et al. |
| 5,417,692 | A | 5/1995 | Goble et al. |
| 5,425,776 | A | 6/1995 | Cohen |
| 5,425,777 | A | 6/1995 | Sarkisian et al. |
| 5,454,814 | A | 10/1995 | Comte |
| 5,464,427 | A | 11/1995 | Curtis et al. |
| 5,474,557 | A | 12/1995 | Mai |
| 5,480,447 | A | 1/1996 | Skiba |
| 5,484,443 | A | 1/1996 | Pascarella et al. |
| 5,507,822 | A | 4/1996 | Bouchon et al. |
| 5,522,903 | A | 6/1996 | Sokolow et al. |
| 5,554,157 | A | 9/1996 | Errico et al. |
| 5,634,925 | A * | 6/1997 | Urbanski ........... A61B 17/7041 606/279 |
| 5,674,297 | A | 10/1997 | Lane et al. |
| 5,702,472 | A | 12/1997 | Huebner |
| 5,725,585 | A | 3/1998 | Zobel |
| 5,782,927 | A | 7/1998 | Klawitter et al. |
| 5,824,095 | A | 10/1998 | Di Maio, Jr et al. |
| 5,876,434 | A | 3/1999 | Flomenblit et al. |
| 5,881,443 | A | 3/1999 | Roberts et al. |
| 5,882,444 | A | 3/1999 | Flomenblit et al. |
| 5,919,193 | A | 7/1999 | Slavitt |
| 5,951,288 | A | 9/1999 | Sawa |
| 5,958,159 | A | 9/1999 | Prandi |
| 5,984,970 | A | 11/1999 | Bramlet |
| 5,984,971 | A | 11/1999 | Faccioli et al. |
| 6,011,497 | A | 1/2000 | Tsang et al. |
| 6,017,366 | A | 1/2000 | Berman |
| 6,146,387 | A | 11/2000 | Trott et al. |
| 6,162,234 | A | 12/2000 | Freedland et al. |
| 6,187,008 | B1 | 2/2001 | Hamman |
| 6,193,757 | B1 | 2/2001 | Foley et al. |
| 6,197,037 | B1 | 3/2001 | Hair |
| 6,200,330 | B1 | 3/2001 | Benderev et al. |
| 6,248,109 | B1 | 6/2001 | Stoffella |
| 6,261,289 | B1 | 7/2001 | Levy |
| 6,319,284 | B1 | 11/2001 | Rushdy et al. |
| 6,342,076 | B1 | 1/2002 | Lundborg |
| 6,352,560 | B1 | 3/2002 | Poeschmann et al. |
| 6,383,223 | B1 | 5/2002 | Baehler et al. |
| 6,386,877 | B1 | 5/2002 | Sutter |
| 6,395,031 | B1 | 5/2002 | Foley et al. |
| 6,423,097 | B2 | 7/2002 | Rauscher |
| 6,428,634 | B1 | 8/2002 | Besselink et al. |
| 6,454,808 | B1 | 9/2002 | Masada |
| 6,475,242 | B1 | 11/2002 | Bramlet |
| 6,554,833 | B2 | 4/2003 | Levy et al. |
| 6,689,169 | B2 | 2/2004 | Harris |
| 6,692,499 | B2 | 2/2004 | Tormala et al. |
| 6,699,247 | B2 | 3/2004 | Zucherman et al. |
| 6,699,292 | B2 | 3/2004 | Ogilvie et al. |
| 6,706,045 | B2 * | 3/2004 | Lin ................... A61B 17/7041 606/264 |
| 6,773,437 | B2 | 8/2004 | Ogilvie et al. |
| 6,811,568 | B2 | 11/2004 | Minamikawa |
| 6,827,741 | B2 | 12/2004 | Reeder |
| 6,833,006 | B2 | 12/2004 | Foley et al. |
| 6,869,449 | B2 | 3/2005 | Ball et al. |
| 6,896,177 | B2 | 5/2005 | Carter |
| 6,981,974 | B2 | 1/2006 | Berger |
| 7,025,789 | B2 | 4/2006 | Chow et al. |
| 7,037,342 | B2 | 5/2006 | Nilsson et al. |
| 7,041,106 | B1 * | 5/2006 | Carver ................. A61F 2/4225 623/21.19 |
| 7,052,498 | B2 | 5/2006 | Levy et al. |
| 7,182,787 | B2 | 2/2007 | Hassler et al. |
| 7,240,677 | B2 | 7/2007 | Fox |
| 7,291,175 | B1 | 11/2007 | Gordon |
| 7,537,664 | B2 | 5/2009 | O'Neill et al. |
| 7,588,603 | B2 | 9/2009 | Leonard |
| 7,600,956 | B2 | 10/2009 | McDuff et al. |
| 7,601,152 | B2 | 10/2009 | Levy et al. |
| 7,655,042 | B2 | 2/2010 | Foley et al. |
| 7,670,339 | B2 | 3/2010 | Levy et al. |
| 7,674,426 | B2 | 3/2010 | Grohowski, Jr. |
| 7,780,737 | B2 | 8/2010 | Bonnard et al. |

(56) References Cited

U.S. PATENT DOCUMENTS

| | | |
|---|---|---|
| 7,837,738 B2 | 11/2010 | Reigstad et al. |
| 7,842,091 B2 | 11/2010 | Johnstone et al. |
| 7,909,880 B1 | 3/2011 | Grant |
| 7,918,879 B2 | 4/2011 | Yeung et al. |
| 7,922,765 B2 | 4/2011 | Reiley |
| 7,955,388 B2 | 6/2011 | Jensen et al. |
| 7,976,580 B2 | 7/2011 | Berger |
| 7,993,403 B2 | 8/2011 | Foley et al. |
| 8,048,173 B2 | 11/2011 | Ochoa |
| 8,100,983 B2 | 1/2012 | Schulte |
| 8,162,942 B2 | 4/2012 | Coati et al. |
| 8,202,305 B2 | 6/2012 | Reiley |
| 8,262,712 B2 | 9/2012 | Coilard-Lavirotte et al. |
| 8,308,779 B2 | 11/2012 | Reiley |
| 8,388,667 B2 | 3/2013 | Reiley et al. |
| 8,394,097 B2 | 3/2013 | Peyrot et al. |
| 8,414,583 B2 | 4/2013 | Prandi et al. |
| 8,414,648 B2 | 4/2013 | Reiley |
| 8,425,570 B2 | 4/2013 | Reiley |
| 8,444,693 B2 | 5/2013 | Reiley |
| 8,470,004 B2 | 6/2013 | Reiley |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 8,715,325 B2 | 5/2014 | Weiner et al. |
| 8,728,387 B2 | 5/2014 | Jones et al. |
| 8,734,462 B2 | 5/2014 | Reiley et al. |
| 8,734,491 B2 | 5/2014 | Seavey |
| 8,834,483 B2 | 9/2014 | Cheney et al. |
| 8,834,572 B2 | 9/2014 | Averous et al. |
| 8,840,623 B2 | 9/2014 | Reiley |
| 8,840,651 B2 | 9/2014 | Reiley |
| 8,858,601 B2 | 10/2014 | Reiley |
| 8,864,804 B2 | 10/2014 | Champagne et al. |
| 8,920,477 B2 | 12/2014 | Reiley |
| 8,986,348 B2 | 3/2015 | Reiley |
| 8,992,703 B2 | 3/2015 | O'Neill et al. |
| 8,998,999 B2 | 4/2015 | Lewis et al. |
| 9,011,504 B2 | 4/2015 | Reed |
| 9,039,743 B2 | 5/2015 | Reiley |
| 9,044,287 B2 | 6/2015 | Reed et al. |
| 9,056,014 B2 | 6/2015 | McCormick et al. |
| 9,072,562 B2 | 7/2015 | Weiner et al. |
| 9,072,564 B2 | 7/2015 | Reed et al. |
| 9,089,427 B2 | 7/2015 | Grohowski, Jr. |
| 9,089,431 B2 | 7/2015 | Grohowski, Jr. |
| D738,504 S | 9/2015 | Weiner et al. |
| 9,125,704 B2 | 9/2015 | Reed et al. |
| 9,135,374 B2 | 9/2015 | Jones et al. |
| 9,161,789 B2 | 10/2015 | Peyrot et al. |
| 9,168,074 B2 | 10/2015 | Prandi et al. |
| 9,180,010 B2 | 11/2015 | Dong et al. |
| 9,283,007 B2 | 3/2016 | Augoyard et al. |
| 9,403,213 B2 | 8/2016 | Lapszynski |
| 9,452,002 B2 | 9/2016 | Roman et al. |
| 9,492,215 B2 | 11/2016 | Augoyard et al. |
| 9,498,266 B2 | 11/2016 | McCormick et al. |
| 9,498,273 B2 | 11/2016 | Thoren et al. |
| 10,022,167 B2 | 7/2018 | Augoyard et al. |
| 2001/0025199 A1 | 9/2001 | Rauscher |
| 2001/0049529 A1 | 12/2001 | Cachia et al. |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0082705 A1 | 6/2002 | Bouman et al. |
| 2002/0169066 A1 | 11/2002 | Cassidy et al. |
| 2003/0040805 A1 | 2/2003 | Minamikawa |
| 2003/0069645 A1 | 4/2003 | Ball et al. |
| 2003/0120277 A1 | 6/2003 | Berger |
| 2003/0130660 A1 | 7/2003 | Levy et al. |
| 2004/0002759 A1 | 1/2004 | Ferree |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0172031 A1* | 9/2004 | Rubecamp ......... A61B 17/8685 606/309 |
| 2004/0220574 A1 | 11/2004 | Pelo et al. |
| 2004/0220678 A1 | 11/2004 | Chow et al. |
| 2005/0065589 A1 | 3/2005 | Schneider et al. |
| 2005/0119757 A1 | 6/2005 | Hassler et al. |
| 2005/0216015 A1 | 9/2005 | Kreidler |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0036322 A1 | 2/2006 | Reiley |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0085075 A1 | 4/2006 | McLeer |
| 2006/0147332 A1 | 7/2006 | Jones et al. |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0156241 A1 | 7/2007 | Reiley et al. |
| 2007/0162018 A1 | 7/2007 | Jensen et al. |
| 2007/0185584 A1 | 8/2007 | Kaufmann et al. |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1* | 6/2008 | Coilard-Lavirotte ....... A61B 17/1604 606/300 |
| 2008/0154385 A1 | 6/2008 | Trail et al. |
| 2008/0177262 A1* | 7/2008 | Augoyard ......... A61B 17/7208 606/280 |
| 2008/0177291 A1* | 7/2008 | Jensen ............... A61B 17/68 606/301 |
| 2008/0195219 A1 | 8/2008 | Wiley et al. |
| 2008/0221697 A1 | 9/2008 | Graser |
| 2008/0221698 A1 | 9/2008 | Berger |
| 2008/0234763 A1 | 9/2008 | Patterson et al. |
| 2008/0269908 A1 | 10/2008 | Warburton |
| 2009/0005821 A1 | 1/2009 | Chirico et al. |
| 2009/0012564 A1 | 1/2009 | Chirico et al. |
| 2009/0138096 A1 | 5/2009 | Myerson et al. |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016905 A1 | 1/2010 | Greenhalgh et al. |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1* | 5/2010 | Peyrot ............... A61B 17/7283 606/300 |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0228301 A1 | 9/2010 | Greenhalgh et al. |
| 2010/0249942 A1 | 9/2010 | Goswami et al. |
| 2010/0256731 A1 | 10/2010 | Mangiardi |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0093084 A1 | 4/2011 | Morton |
| 2011/0093085 A1 | 4/2011 | Morton |
| 2011/0144644 A1 | 6/2011 | Prandi et al. |
| 2011/0208304 A1 | 8/2011 | Justin et al. |
| 2011/0301652 A1 | 12/2011 | Reed et al. |
| 2012/0029579 A1 | 2/2012 | Bottlang et al. |
| 2012/0065692 A1 | 3/2012 | Champagne et al. |
| 2012/0089197 A1 | 4/2012 | Anderson |
| 2012/0259419 A1 | 10/2012 | Brown et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0123862 A1 | 5/2013 | Anderson et al. |
| 2013/0131822 A1 | 5/2013 | Lewis et al. |
| 2013/0150965 A1 | 6/2013 | Taylor et al. |
| 2013/0190761 A1 | 7/2013 | Prandi et al. |

(56) References Cited

U.S. PATENT DOCUMENTS

| | | |
|---|---|---|
| 2013/0190831 A1 | 7/2013 | Ek et al. |
| 2013/0231744 A1 | 9/2013 | Taylor et al. |
| 2013/0317559 A1 | 11/2013 | Leavitt et al. |
| 2013/0325077 A1 | 12/2013 | Champagne et al. |
| 2014/0005219 A1 | 1/2014 | Foster et al. |
| 2014/0039630 A1 | 2/2014 | Peyrot et al. |
| 2014/0058462 A1 | 2/2014 | Reed et al. |
| 2014/0107712 A1 | 4/2014 | Fallin et al. |
| 2014/0142715 A1 | 5/2014 | McCormick |
| 2014/0180428 A1 | 6/2014 | McCormick |
| 2014/0188239 A1 | 7/2014 | Cummings |
| 2014/0257509 A1 | 9/2014 | Dacosta et al. |
| 2014/0276827 A1 | 9/2014 | Roman et al. |
| 2014/0277554 A1 | 9/2014 | Roman et al. |
| 2014/0309747 A1 | 10/2014 | Taylor et al. |
| 2014/0316474 A1 | 10/2014 | Graham |
| 2014/0343615 A1 | 11/2014 | Cheney et al. |
| 2015/0011998 A1* | 1/2015 | McCormick ........ A61F 5/05875 606/56 |
| 2015/0066097 A1 | 3/2015 | Biedermann |
| 2015/0073413 A1 | 3/2015 | Palmer et al. |
| 2015/0094778 A1 | 4/2015 | McCormick et al. |
| 2015/0112341 A1 | 4/2015 | Penzimer et al. |
| 2015/0112342 A1* | 4/2015 | Penzimer ........... A61B 17/7291 606/63 |
| 2015/0112446 A1 | 4/2015 | Melamed et al. |
| 2015/0150607 A1 | 6/2015 | Chen et al. |
| 2015/0164563 A1 | 6/2015 | Lewis et al. |
| 2015/0223848 A1 | 8/2015 | McCormick |
| 2015/0223850 A1 | 8/2015 | Reed |
| 2015/0223853 A1 | 8/2015 | Appenzeller et al. |
| 2015/0342655 A1 | 12/2015 | Reed et al. |

FOREIGN PATENT DOCUMENTS

| | | |
|---|---|---|
| CA | 2836654 A1 | 6/2014 |
| CA | 2837497 A1 | 6/2014 |
| EP | 0042808 A1 | 12/1981 |
| EP | 0340159 A1 | 11/1989 |
| EP | 0420794 A1 | 4/1991 |
| EP | 0454645 A1 | 10/1991 |
| EP | 1300122 A2 | 4/2003 |
| EP | 1356794 A3 | 11/2003 |
| EP | 1582159 A1 | 10/2005 |
| EP | 1923012 A1 | 5/2008 |
| EP | 2228015 A3 | 3/2011 |
| EP | 2471477 A1 | 7/2012 |
| EP | 2471478 A1 | 7/2012 |
| EP | 2544633 A1 | 1/2013 |
| EP | 2749236 A3 | 10/2014 |
| FR | 2663838 A1 | 1/1992 |
| FR | 2725126 A1 | 4/1996 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2856269 A1 | 12/2004 |
| FR | 2884406 | 10/2006 |
| FR | 2927529 A1 | 8/2009 |
| FR | 2935601 A1 | 3/2010 |
| FR | 2957244 A1 | 9/2011 |
| GB | 2119655 A | 11/1983 |
| GB | 2430625 B | 4/2007 |
| JP | S60145133 A | 7/1985 |
| JP | 03001854 A | 8/1991 |
| JP | H7303662 A | 11/1995 |
| JP | 2004535249 A | 11/2004 |
| JP | 3648687 B2 | 5/2005 |
| JP | 2007530194 A | 11/2007 |
| JP | 2008188411 A | 8/2008 |
| JP | 2008537696 A | 9/2008 |
| JP | 4695511 B2 | 6/2011 |
| JP | 5631597 B2 | 11/2014 |
| JP | 5645826 B2 | 12/2014 |
| KR | 20070004513 A | 1/2007 |
| KR | 20070022256 A | 2/2007 |
| KR | 101004561 B1 | 1/2011 |
| KR | 101235983 B1 | 2/2013 |
| WO | 9116014 A1 | 10/1991 |
| WO | 9625129 A1 | 8/1996 |
| WO | 9641596 A1 | 12/1996 |
| WO | 9726846 A1 | 7/1997 |
| WO | 9733537 A1 | 9/1997 |
| WO | 0117445 A1 | 3/2001 |
| WO | 03084416 A1 | 10/2003 |
| WO | 2005/020831 A2 | 3/2005 |
| WO | 2005020830 A1 | 3/2005 |
| WO | 2005063149 A1 | 7/2005 |
| WO | 2005104961 A1 | 11/2005 |
| WO | 2006109004 A1 | 10/2006 |
| WO | 2007/135322 A1 | 11/2007 |
| WO | 2008057404 A2 | 5/2008 |
| WO | 2008112308 A1 | 9/2008 |
| WO | 2008129214 A2 | 10/2008 |
| WO | 2009055952 A1 | 5/2009 |
| WO | 2009103085 A1 | 8/2009 |
| WO | 2010029246 A1 | 3/2010 |
| WO | 2011082343 A1 | 7/2011 |
| WO | 2011110784 A1 | 9/2011 |
| WO | 2011116078 A1 | 9/2011 |
| WO | 2011130229 A1 | 10/2011 |
| WO | 2012089330 A1 | 7/2012 |
| WO | 2012089331 A1 | 7/2012 |
| WO | 2013164819 A1 | 11/2013 |
| WO | 2014031947 A1 | 2/2014 |
| WO | 2014165123 A1 | 10/2014 |
| WO | 2015136212 A1 | 9/2015 |

OTHER PUBLICATIONS

HammerFix IP Fusion System, Hammertoe Deformity Surgical Technique, designed by Extremity Medical, published Mar. 31, 2014 (8 pages).

International Search Report for PCT/FR2008/050453 dated Nov. 4, 2008, 4 pages.

International Search Report, PCT/FR2006/050345, dated Aug. 30, 2006, 3 pages.

Intraosseous Fixation System, Hammertoe Surgical Technique, designed by OrthoHelix, published Aug. 23, 2012 (16 pages).

Japanese Office Action for Application No. 2011-526540 dated Aug. 13, 2013, 3 pages.

Pietrzak WS, et al., "A bioabsorbable fixation implant for use in proximal interphalangeal joint (hammer toe) arthrodesis: Biomechanical testing in a synthetic bone substrate". J Foot Ankle Surg. Sep.-Oct. 2006;45(5):288-94. doi: 10.1053/j.jfas.2006.05.004. PMID: 16949524. 7 pgs. [Exhibit No. 1007 to Petition for Inter Partes Review of U.S. Pat. No. 9,168,074].

The American Heritage College Dictionary, Fourth Edition, Houghton Mifflin Company (Apr. 2007). 3 pgs. [Exhibit No. 1008 to Petition for Inter Partes Review of U.S. Pat. No. 9,168,074].

Cross section, https://byjus.com/maths/cross-section/ (last visited Jan. 26, 2022). 4 pgs. [Exhibit No. 1009 to Petition for Inter Partes Review of U.S. Pat. No. 9,168,074].

Declaration of Michael Sherman (Jan. 28, 2022). 119 pgs. [Exhibit No. 1002 to Petition for Inter Partes Review of U.S. Pat. No. 9,168,074].

Petition for Inter Partes Review of U.S. Pat. No. 9,168,074, *OsteoMed LLC v. Stryker European Operations Holdings LLC.* (Jan. 28, 2022). 98 pgs.

Patent Owner's Preliminary Response and Exhibits List, IPR2022-00486 of U.S. Pat. No. 9,168,074, *OsteoMed LC v. Stryker European Operations Holdings LLC.* (Filed May 16, 2022), 77 pages. [Including Appendices at Exhibits 2003 and 2004].

Collins English Dictionary Excerpt (Jun. 2007), 6 pages. [Exhibit No. 2001 to Patent Owner's Preliminary Response, IPR2022-00486 of U.S. Pat. No. 9,168,074 filed May 16, 2022].

Excerpt from Tool.com—File and Rasp Tools, (Copyright 2022), 6 pages. [Exhibit No. 2002 to Patent Owner's Preliminary Response, IPR2022-00486 of U.S. Pat. No. 9,168,074 filed May 16, 2022].

(56) References Cited

OTHER PUBLICATIONS

Jung, H. J. et al., JJ., Decision Denying Institution of Inter Partes Review, IPR2022-00486 of U.S. Pat. No. 9,168,074 , *OsteoMed LLC* v. *Stryker European Operations Holdings LLC*. (Aug. 12, 2022). 42 pages.

* cited by examiner

RESORPTIVE INTRAMEDULLARY IMPLANT BETWEEN TWO BONES OR TWO BONE FRAGMENTS

CROSS-REFERENCE TO RELATED APPLICATIONS

This application is a continuation of U.S. patent application Ser. No. 14/858,855, filed Sep. 18, 2015, which is a divisional of U.S. patent application Ser. No. 13/795,946, filed Mar. 12, 2013, now U.S. Pat. No. 9,168,074, which is a continuation of U.S. patent application Ser. No. 12/918,105, filed Oct. 29, 2010, now U.S. Pat. No. 8,414,583, which application is a U.S. national phase entry under 35 U.S.C. § 371 of International Application No. PCT/FR2009/051658, filed Sep. 2, 2009, published as WO 2010/029246, which claims priority from French Patent Application No. 0856035, filed Sep. 9, 2008, whose entire disclosures are herewith incorporated by reference.

FIELD OF THE INVENTION

The invention relates to the technical field of orthopedic implants, particularly for arthrodesis and osteosynthesis.

More particularly, the invention relates to an intramedullary implant for arthrodesis between two bone parts or osteosynthesis between two bone fragments, particularly in the case of the hand or foot.

BACKGROUND OF THE INVENTION

Different solutions have been proposed to achieve these functions.

For example, a solution comes from the teaching of patent application FR 2,884,406 [US 2008/0177262], of which the applicant of the present application is also the applicant. This patent describes an intramedullary osteosynthesis device constituted of an elongated body whose ends constitute anchor zones cooperating with the bone parts to be immobilized. The anchor zones are shaped and made of a material selected to enable insertion into the bone parts, then to ensure an anchor in the bone parts by preventing any rotational movement by resisting traction and by maintaining a compression force.

Another solution also comes from patent application FR 07.02003 [US 2010/0131014], also from the same applicant. This document describes an implant in the form of two anchor zones connected by a central zone and whose general shape is substantially inscribed in a very elongated rectangle of X-shape, so as to form in the anchor zones two legs adapted to move apart by elastic or shape-memory effect.

From this design, different criteria have been established to make the implant easy to place and efficient in order to create a primary and secondary stability for the osteosynthesis or arthrodesis site.

However, these solutions are not adapted for the case of an implant made of resorptive material.

BRIEF SUMMARY OF THE INVENTION

From this state of the art, the object that the invention proposes to attain is further improving the anchor and the stability of the implant as well as its adaptation to the morphology of the implantation site when the implant is made of resorptive material.

To solve such a problem, a resorptive intramedullary implant between two bones or two bone fragments has been designed and developed; it is constituted, in a known manner, of a single-piece body having a general elongated shape with, at each end, zones for anchoring to the bone parts being considered. According to the invention, one of the zones has a cylindrical shape, whereas the other zone is flat.

Advantageously, the implant is made of a resorptive material whose mechanical properties are determined to last the time necessary for the consolidation, so that the implant is resorbed after six months. For example, the implant is composed of lactic acid polymer or copolymer (PLA, PGA . . . ).

Considering the specific mechanical characteristics of resorptive materials, and to solve the given problem of improving anchor and stability, the cylindrical cross-section is threaded and tapers in the direction of its free end.

To solve the given problem of enabling a deformation by elasticity, thus causing an expansion adapted to the geometry of the site and to the properties of the material, the flat cross-section zone has, substantially in its median portion, an opening adapted to enable elastic deformation of the zone. The opening defines at least two anchor arms.

It therefore appears that the combination of a cylindrical and threaded anchor zone and a flat-sectioned anchor zone is particularly advantageous considering the problem to be solved.

To solve the given problem of resisting the shear and flexion forces susceptible of occurring in the area of the bone site, between the two anchor zones, the body has a central zone of transition adapted to resist the shear and flexion forces occurring in the area of the bone site and adapted to serve as an abutment.

From this basic design of the implant, the anchor zones are either coaxial or angularly offset by between about 1° and 30° and, advantageously, by 10°. The bend between the anchor zones is located so as to substantially correspond to an arthrodesis line of the bones being considered.

BRIEF DESCRIPTION OF THE DRAWINGS

The invention is explained in more detail hereinafter with reference to the attached drawings, in which.

DETAILED DESCRIPTION

The implant according to the invention has a one-piece body 1 of elongated shape and having a first proximal zone A1 and a second distal zone A2. The entire implant body is made of a resorptive material whose mechanical properties are determined for the implant to be resorbed in no less than about 6 months. In one embodiment, the implant is composed of lactic acid polymer or copolymer (PLA, PGA . . . ).

As will be described later in the description, the zones A1 and A2 have anchor formations for the respective bone parts. Taking into account the specific characteristics of the resorptive material and to attain the given object of anchor and stability, the zone A1 is of a cylindrical shape section whereas the other zone A2 is flat.

The zone A1 has a generally cylindrical outer surface 1a with a limited taper toward its free end. The surface 1a has a helical rib forming a screwthread 1a1.

The zone A2 is flat and has substantially in its center, an opening 1b adapted to enable elastic deformation of the zone A2. More particularly, the opening 1b defines at least two anchor arms 1c and 1d, each having at least one outwardly projecting tooth 1c1, 1d1.

Advantageously, between the two zones A1 and A2 the body 1 has a central zone C for transition adapted to resist shear and flexion forces that can occur at the end of a bone. By way of nonlimiting example, this median zone C can have a length of about 3.5 mm and a thickness of about 2 mm, for an overall implant length comprised between about 15 and 25 mm and a diameter of about 2 or 3 mm at the zone A1.

Figure 1:
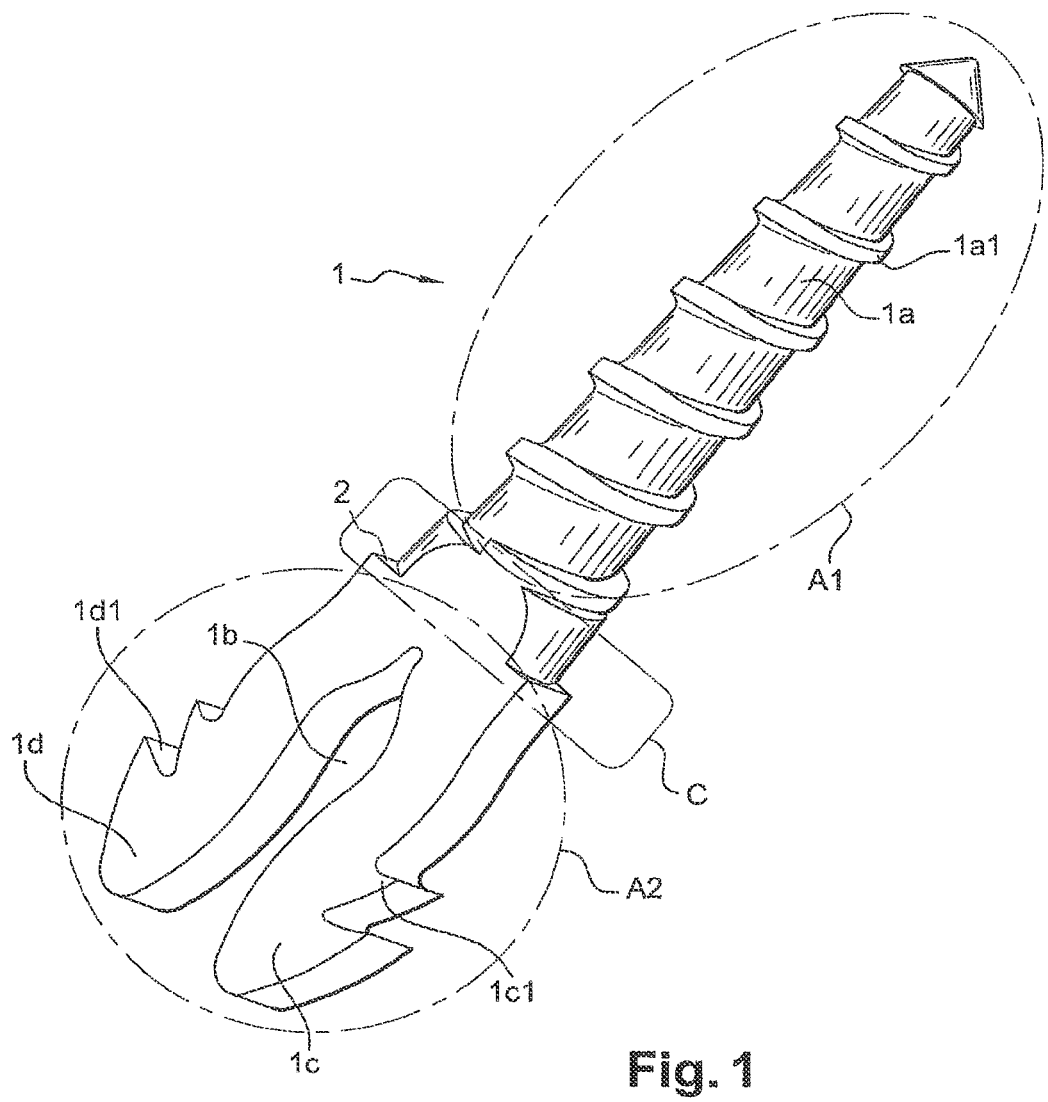
FIG. 1 is a perspective view of the implant.
Figure 3:
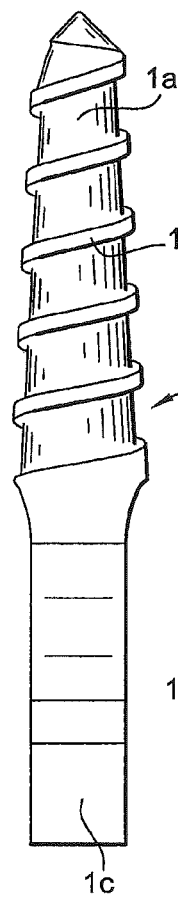
FIG. 3 is a side view corresponding to FIG. 2.
Figure 2:
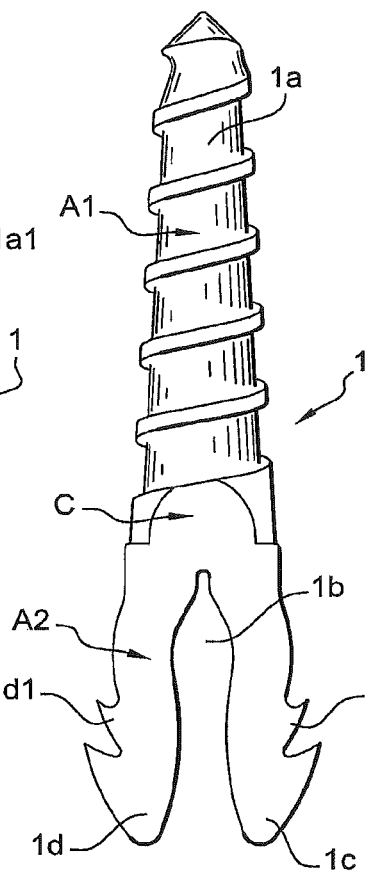
FIG. 2 is a front view of the implant before insertion into the bone part in question.
Figure 4:
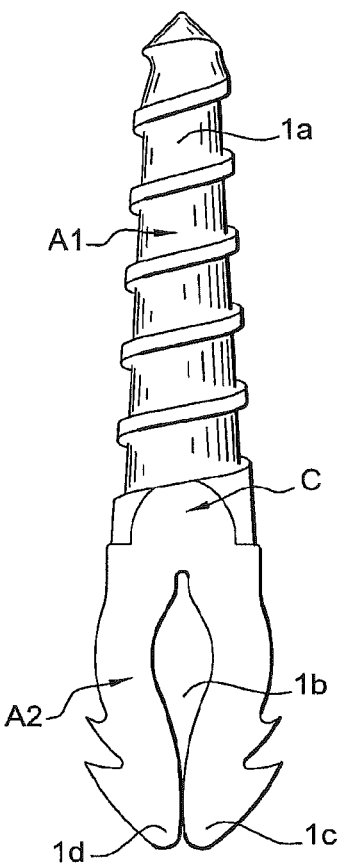
FIG. 4 is a view like FIG. 2 showing the position of the anchor arms of the flat section after insertion.

In the embodiment shown in FIG. 1, the two zones A1 and A2 are coaxial.

Figure 5:
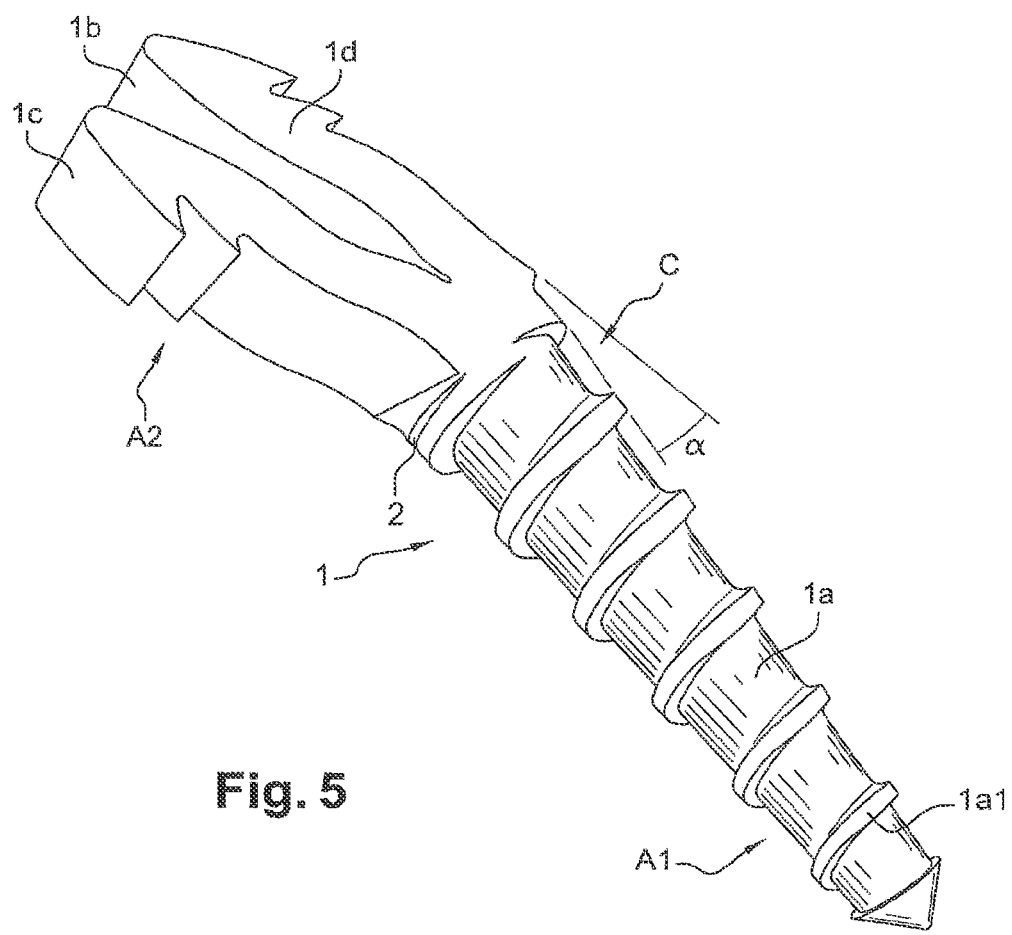
FIG. 5 is a perspective view of another advantageous embodiment of the implant.

To solve the problem of adaptation to the shape of the implantation site, the anchor zones A1 and A2 can be offset at an angle α adapted to the geometry of the bone site. This angle α is comprised between about 1° and 30° and, advantageously, on the order of 10° when the implant is for foot arthrodesis (FIG. 5).

In this embodiment in which the two anchor zones are angularly offset, the bend is located so as to correspond substantially to the arthrodesis line of the bone parts being fused.

Figure 6:
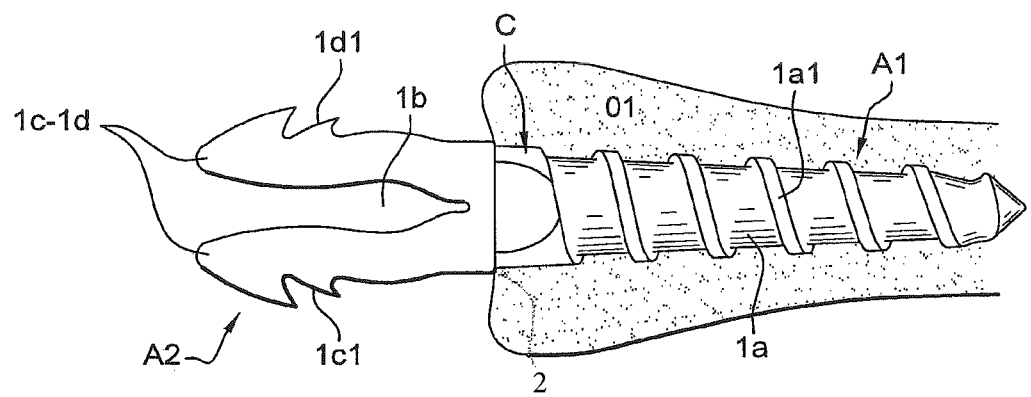
FIGS. 6 and 7 show the installation of the implant into two bone parts.
Figure 7:
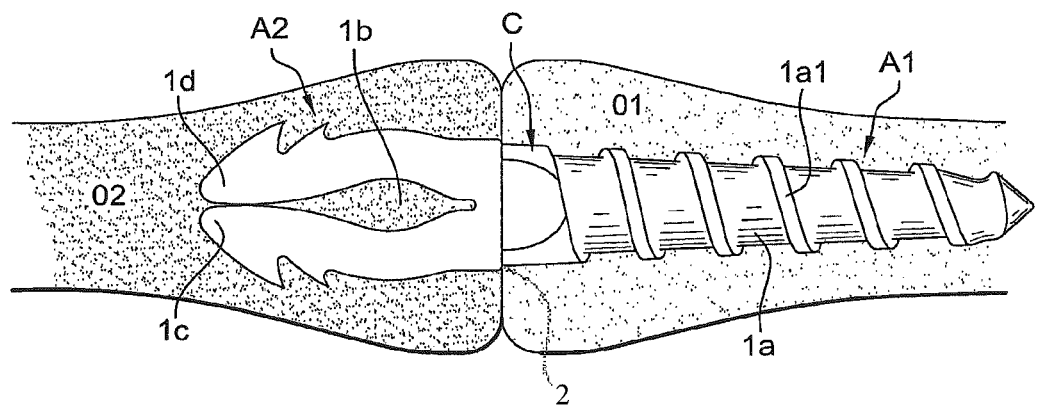

FIGS. 6 and 7 schematically show the positioning of the implant according to the invention between two bone parts O1 and O2. After suitable holes have been made in the bone by a rasp-type tool, the operator screws the thread 1a into the bone part O1 substantially up to step 2 of the median zone C providing a surface that, as shown, faces towards thread 1a in a direction parallel to a longitudinal axis defined by zones A1, A2 and serves as an abutment preventing the implant from sinking too deeply into the bone (see FIGS. 1, 5, 6, and 7). The operator then fits the second bone part O2 back onto the anchor arms 1d and 1c of the zone A2, the anchor arms then spread and tighten by elasticity (FIG. 7).

The operative technique can be the following:
Drilling of the two holes with a conventional drill;
Preparation of the holes with a rasp for the flat side and a bone tap to form the inner screw thread on the cylindrical side;
Use of a screwdriver with a gripper end;
Screwing in the cylindrical side P1 [A1] for an arthrodesis IPP of the foot;
Fitting of the bone back onto the flat side [A2] of the implant.

The advantages are readily apparent from the description; in particular, it is to be emphasized and understood that the combination of the two anchor zones A1 and A2 of cylindrical and a flat shape, respectively, significantly enhances anchor and stability of the implant adapted to the geometry of the bone site and to the material properties, namely, a resorptive material.

The invention claimed is:

1. An intramedullary implant for insertion into first and second bone parts, the implant being a one-piece body, the one-piece body comprising:
a threaded first end for anchoring to the first bone part; and
a second end extending from the first end for anchoring to the second bone part, the second end comprising:
a body portion defining a longitudinal axis thereof;
a first arm and a second arm projecting from the body portion;
a first projection and a second projection spaced apart from the first projection, the first and the second projections extending from the first arm away from the longitudinal axis; and
a third projection extending from the second arm in a different direction than the first projection,
wherein the second end extends from the first end to form a step, the step having a surface facing in a direction parallel to the longitudinal axis and away from the second end.

2. The intramedullary implant of claim 1, wherein the third projection extends in a different direction than the second projection extends from the first arm.

3. The intramedullary implant of claim 1, wherein a fourth projection spaced apart from the third projection extends from the second arm.

4. The intramedullary implant of claim 1, wherein the first and the second projections extend in a same direction.

5. The intramedullary implant of claim 1, wherein the step defines a plane perpendicular to the longitudinal axis.

6. The intramedullary implant of claim 1, wherein entireties of the first and the second arms are spaced from the longitudinal axis to define an opening therebetween.

7. The intramedullary implant of claim 1, wherein the intramedullary implant is made of a polymer.

8. The intramedullary implant of claim 1, wherein the first projection includes a first flat portion, the second projection includes a second flat portion, and the third projection includes a third flat portion, and wherein the first, the second, and the third flat portions are coplanar.

9. The intramedullary implant of claim 1, wherein the first projection includes first and second opposing surface portions, the second projection includes third and fourth opposing surface portions, and the third projection includes fifth and sixth opposing surface portions, and wherein each of the first, the third, and the fifth opposing surface portions define a first plane and each of the second, the fourth, and the sixth opposing surface portions define a second plane parallel to the first plane.

10. An intramedullary implant for insertion into first and second bone parts, the implant being a one-piece body, the one-piece body comprising:
a threaded first end for anchoring to the first bone part; and
a second end extending from the first end for anchoring to the second bone part, the second end comprising:
a body portion defining an opening in a median portion thereof;
a first plurality of projections extending from a first side of the body portion and extending away from the opening, each one of the first plurality of projections including a respective one of a first set of flat surface portions, the first set of flat surface portions being coplanar; and
a second plurality of projections extending from a second side of the body portion opposite the first side and extending away from the opening, each one of the second plurality of projections including a respective one of a second set of flat surface portions, the second set of flat surface portions being coplanar.

11. The intramedullary implant of claim 10, wherein the projections of the first plurality of projections extend away from the opening in a same direction.

12. The intramedullary implant of claim 11, wherein the projections of the second plurality of projections extend away from the opening in a same direction.

13. The intramedullary implant of claim 10, wherein the body portion includes a pair of arms and the opening is defined by the pair of arms.

14. The intramedullary implant of claim 10, wherein the body portion defines a longitudinal axis, and wherein the second end extends from the first end to form a step defining a plane perpendicular to the longitudinal axis.

15. The intramedullary implant of claim 10, wherein the intramedullary implant is made of a polymer.

16. The intramedullary implant of claim 10, wherein the first and the second sets of flat surface portions are coplanar.

17. The intramedullary implant of claim 10, wherein the first and the second sets of flat surface portions are coplanar.

18. The intramedullary implant of claim 17, wherein the first plurality of projections include a third set of flat surface portions opposite respective ones of the first set of flat surface portions, the third set of flat surface portions being coplanar, and wherein the second plurality of projections include a fourth set of flat surface portions opposite respective ones of the second set of flat surface portions, the fourth set of flat surface portions being coplanar, and wherein each of the first, the second, the third, and the fourth sets of flat surface portions lie in parallel planes.

19. An intramedullary implant for insertion into first and second bone parts, the implant being a one-piece body, the one-piece body comprising:
   a threaded first end for anchoring to the first bone part; and
   a second end extending from the first end for anchoring to the second bone part, the second end having a body portion, a first projection extending from a first side of the body portion, a second projection extending from a second side of the body portion opposite the first side, and a third projection extending from the first side of the body portion in a direction away from a longitudinal axis defined by the body portion, the first and the second projections extending in different directions away from the longitudinal axis and the third projection being spaced from the first projection,
   wherein the second end extends from the first end to form a step defining a plane perpendicular to the longitudinal axis, the step having a surface facing in a direction parallel to the longitudinal axis and away from the second end,
   wherein the first projection includes first and second opposing surface portions, the second projection includes third and fourth opposing surface portions, and the third projection includes fifth and sixth opposing surface portions, and
   wherein each of the first, the third, and the fifth opposing surface portions define a first plane and each of the second, the fourth, and the sixth opposing surface portions define a second plane parallel to the first plane.

20. The intramedullary implant of claim 19, wherein the first and the second projections are in alignment relative to and spaced apart from the longitudinal axis.

21. The intramedullary implant of claim 19, wherein the second end includes separated arms defining an opening, and wherein each of the first and the second projections extends from the separated arms.

* * * * *